US009545225B2

(12) United States Patent
Cavuoto et al.

(10) Patent No.: US 9,545,225 B2
(45) Date of Patent: Jan. 17, 2017

(54) DEVICE-INDEPENDENT NEUROLOGICAL MONITORING SYSTEM

(71) Applicant: James Cavuoto, Truckee, CA (US)

(72) Inventors: James Cavuoto, Truckee, CA (US); Tony Gaitatzis, Walnut Creek, CA (US)

(73) Assignee: James Cavuoto, Truckee, CA (US)

( * ) Notice: Subject to any disclaimer, the term of this patent is extended or adjusted under 35 U.S.C. 154(b) by 0 days.

(21) Appl. No.: 14/545,288

(22) Filed: Apr. 16, 2015

(65) Prior Publication Data

US 2015/0366497 A1 Dec. 24, 2015

Related U.S. Application Data

(63) Continuation-in-part of application No. 13/507,067, filed on Jun. 1, 2012, now abandoned.

(60) Provisional application No. 61/519,964, filed on Jun. 2, 2011.

(51) Int. Cl.
| | |
|---|---|
| *A61B 5/04* | (2006.01) |
| *A61B 5/16* | (2006.01) |
| *A61B 5/0476* | (2006.01) |
| *A61B 5/00* | (2006.01) |
| *G09B 19/00* | (2006.01) |

(52) U.S. Cl.
CPC ............. *A61B 5/165* (2013.01); *A61B 5/0006* (2013.01); *A61B 5/0476* (2013.01); *A61B 5/7246* (2013.01); *G09B 19/00* (2013.01); *A61B 5/0022* (2013.01); *G10H 2220/376* (2013.01); *G10H 2240/085* (2013.01)

(58) Field of Classification Search
None
See application file for complete search history.

(56) References Cited

U.S. PATENT DOCUMENTS

| | | | | |
|---|---|---|---|---|
| 2005/0273890 | A1* | 12/2005 | Flaherty | A61B 5/0031 600/544 |
| 2006/0217628 | A1* | 9/2006 | Huiku | A61B 5/02 600/544 |
| 2010/0063411 | A1* | 3/2010 | Donoghue | G06F 19/3412 600/545 |
| 2011/0071416 | A1* | 3/2011 | Terada | A61B 5/0478 600/544 |
| 2011/0245708 | A1* | 10/2011 | Finkel | A61B 5/0484 600/544 |

OTHER PUBLICATIONS

"Electroencephalogy," in "Bioelectromagnetism: Principles and Applications of Bioelectric and Biomagnetic Fields," by Jaakko Malmivuo and Robert Plonsey (Oxford University Press, New York, 1995), Chapter 13.

(Continued)

*Primary Examiner* — Etsub Berhanu
(74) *Attorney, Agent, or Firm* — Steven Stupp

(57) ABSTRACT

A system that analyzes neurological signals is described. During operation, the system monitors neurological signals from users at multiple locations, where the neurological signals are associated with different electrode configurations. Then, the system modifies the monitored neurological signals to correct for the different electrode configurations so that a resulting set of modified neurological signals corresponds to a common electrode configuration, thereby facilitating subsequent identification of a subset of the set of modified neurological signals.

20 Claims, 10 Drawing Sheets

(56) References Cited

OTHER PUBLICATIONS

Roberto D. Pascual-Marqui, "Assessing interactions in the brain with exact low-resolution electromagnetic tomography," Phil. Trans. R. Soc. A (2011) vol. 369, pp. 3768-3784.
"Integral Equations and Green's Functions," by Ronald B Guenther and John W Lee, in Chapter 4 of "Partial Differential Equations of Mathematical Physics and Integral Equations" (Dover Publications, New York, 1988) and in "Methods of Applied Mathematics," second edition, Francis B. Hildebrand (Prentice-Hall, Englewood-Cliffs, NJ, 1952), pp. 228-241.

\* cited by examiner

DEVICE-INDEPENDENT NEUROLOGICAL MONITORING SYSTEM

CROSS REFERENCE TO RELATED APPLICATIONS

This application claims priority under 35 U.S.C. 120 as a Continuation-in-Part Patent Application of U.S. patent application Ser. No. 13/507,067, "Device-Independent Neurological Monitoring System," by James Cavuoto, filed on Jun. 1, 2012, which claim priority under 35 U.S.C. 119(e) to U.S. Provisional Application Ser. No. 61/519,964, "Device-Independent Neurological Monitoring System," by James Cavuoto, filed an Jun. 2, 2011, the contents of each of which are herein incorporated by reference.

BACKGROUND

The present disclosure relates to techniques for a system for collecting neurological signals using different electrode or sensor configurations from users at multiple locations.

Neurological monitoring and stimulation is increasingly popular. For example, driven by the lower cost and increased availability of electrodes and sensors companies are exploring neuromarketing in which neurological data is collected from users while the users engage in activities, such as in a focus group. However, in order to collect the neurological data, these companies are often forced to bring the users to a common location, where a standard type of electrode or sensor model is used to monitor the users. This approach can be cumbersome and expensive. Consequently, it can restrict the number of users that participate, which may bias the collected neurological data.

SUMMARY

The disclosed embodiments relate to a system (such as a computer system) that analyzes neurological signals. During operation, the system monitors neurological signals from users at multiple separate locations, where the neurological signals are associated with different electrode configurations. Then, the system modifies the monitored neurological signals to correct for the different electrode configurations so that a resulting set of modified neurological signals corresponds to a common electrode configuration so that a subset of the set of modified neurological signals can be identified.

In some embodiments, the system determines a neurological signature (such as EEG signals associated with a psychological state and/or a physical activity) characteristic of a behavior exhibited or performed by multiple individuals corresponding to the monitored neurological signals, where the neurological signature includes a subset of the set of modified neurological signals; and provides a recommendation to guide improvement of the behavior based on the neurological signature.

Note that the different electrode configurations may include: different types of electrodes, such as different electrode models provided by different manufacturers; different spatial sampling rates; and/or different electrode positions on the users.

Moreover, the neurological signals may include electroencephalogram signals.

Furthermore, the modifying may involve: interpolating between the monitored neurological signals associated with a pair of adjacent electrodes in a given electrode configuration; interpolating between the monitored neurological signals associated with the pair of adjacent electrodes in the given electrode configuration based on the neurological signals associated with at least another electrode in the given electrode configuration; extrapolating the monitored neurological signals associated with at least a subset of the electrodes in the given electrode configuration; implied data correlation; and/or duplication of at least some of the monitored neurological signals.

In some embodiments, the system analyzes the modified neurological signals based on physiological responses of the users to external stimuli to identify the subset of the set of modified neurological signals. For example, the external stimuli may be displayed audio video information and the physiological responses may include: a behavior, an emotional response, a vital sign, a motion, an ability to perform a task, etc.

Another embodiment provides a method that includes at least some of the operations performed by a system.

Another embodiment provides a computer-program product for use with the system. This computer-program product includes instructions for at least some of the operations performed by the system.

BRIEF DESCRIPTION OF THE FIGURES

Note that like reference numerals refer to corresponding parts throughout the drawings. Moreover, multiple instances of the same part are designated by a common prefix separated from an instance number by a dash.

DETAILED DESCRIPTION

Figure 1:
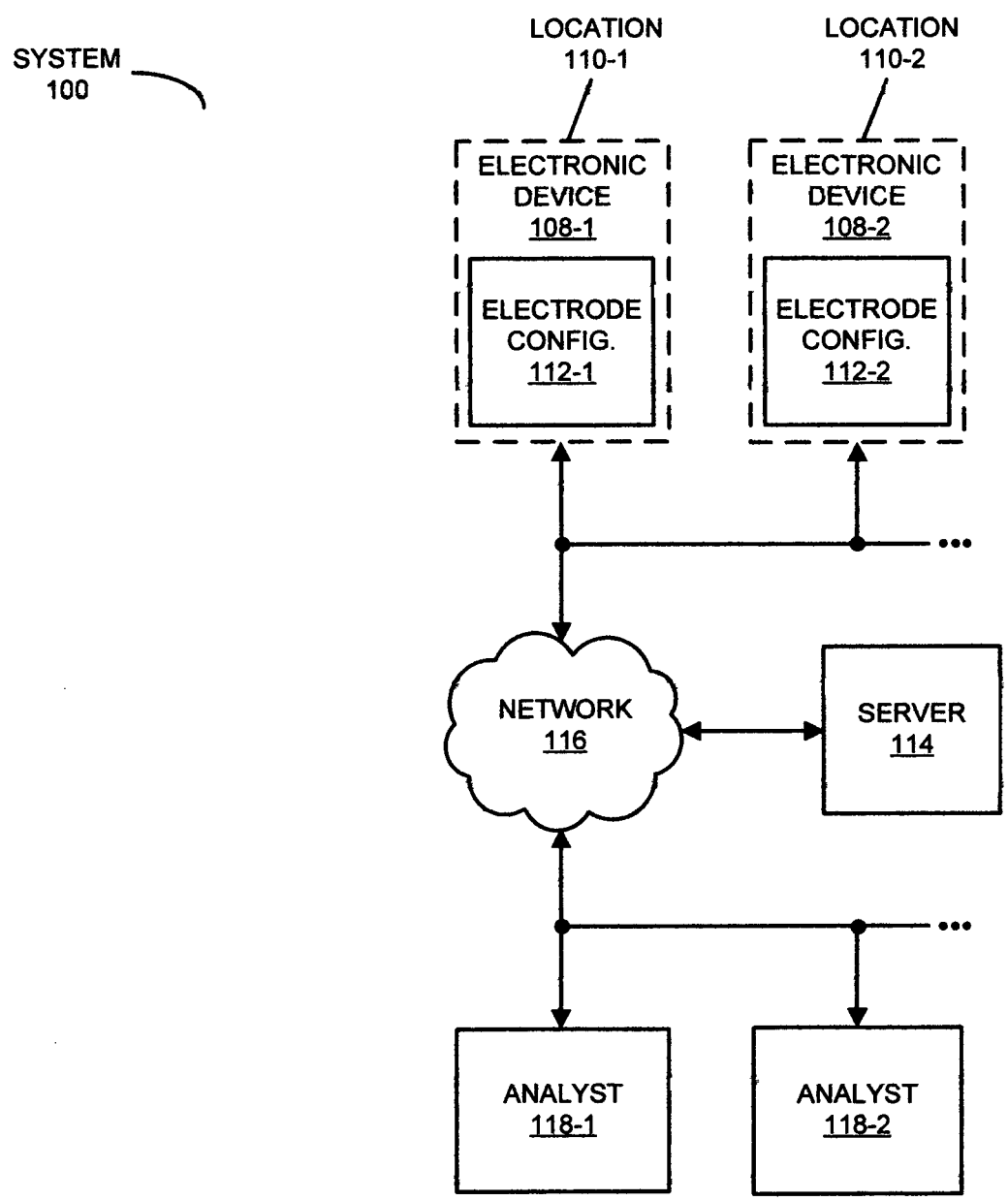
FIG. 1 is system in accordance with an embodiment of the present disclosure.

A system for multi-user interactive physiological monitoring/stimulation is described. As shown in FIG. 1, in this system neurological signals for (or brainwave data) may be measured from or neurological stimulation may be applied to users at multiple separate locations 110 via electronic devices 108 (such as computers) and electrode configurations 112. For example, the measured neurological signals or the generated neurological stimulation may utilize: wireless electroencephalogram (EEG) headsets, brain-computer interfaces, etc. These measurements and/or stimulations may occur when the users interact with content, such as: text, pictures, video, music, sound, advertisements, sensory stimuli, video games, augmented reality, virtual reality, etc. In addition, the measurements may include: user feedback about the content, such as: approval, disapproval, descriptions, classifications, emotional responses, etc. In some embodiments, the measurements include user physiological data, such as vital signs, temperature, perspiration, behaviors, motions or bodily displacements, ability to perform one or more tasks or activities, etc.

Moreover, system 100 may be able to concurrently accommodate a wide variety of electrode configurations 112 at locations 110, such: as different types of electrodes (or sensors), different electrode positions relative to anatomical features of the users (e.g., different positions of the electrodes on the users' heads), different spatial sampling (i.e., different numbers of electrodes or sensors), etc. For example, the measured neurological signals and user feedback from different locations 110 may be collected by server 114 via network 116. (This data collection may be in real time. Alternatively, electronic devices 108 may collect data for a time interval and then may communicate the collected neurological signals to server 114 via network 116.) Then, server 114 may scale (for example, using dynamic time warping), re-sample, remap, normalize, etc. the measured neurological signals to generate modified neurological signals. Therefore, in effect, system 100 may operate in a device-independent manner.

The modified neurological signals can then be analyzed and compared to each other. In particular, server 114 may make the user feedback, the physiological data, the measured neurological signals and/or the modified neurological signals available to different (and, possibly, independent) analysts 118 via network 116. For example, analysts 118 may include: sponsors, researchers, other users, etc. Note that these analysts may analyze the data to identify statistical associations between one or more neurological signals (which are sometimes referred to as 'neurological signatures,' 'physiological events' or 'biomarkers') and the user feedback and/or the physiological data. (Thus, the identification may involve one or more supervised learning techniques, as is known to one of skill in the art.) More generally, system 100 may provide a supervised learning environment in which neurological signatures associated with behaviors (such as psychological states, emotions, thoughts and/or physical activities of the users) can be determined. For example, the modified neurological signals may be associated with a behavior that is repeated multiple times by one or more users. The modified neurological signals associated with multiple instances of the behavior may be combined or averaged together to improve the signal-to-noise ratio, and the correlation with the timing of the behavior may be used to identify a neurological signature using a supervised learning technique (such as a classification and regression tree, a support vector machine, Lasso, a neural network). Alternatively, in some embodiments an unsupervised learning technique (such as clustering) is used.

In this way, system 100 may enable users to share data, such as brainwave data, with each other or analysts 118 either in real time, or to aggregate and store such data for later analysis and use.

In an exemplary embodiment, the users may listen to music. Using electrode configurations 112 that are provided by different manufacturers and vendors, the users may monitor their neurological signals while listening to the music. In addition, the users may classify their emotional response to the music by concurrently selecting descriptive adjectives from a finite set of descriptive adjectives (which is the user feedback in this example), for example, using a software program that is installed on and which executes in environments of electronic devices 108. These neurological signals and the descriptive adjectives may be collected and processed by server 114. Then, analysts 118 may analyze the data in an attempt to identify one or more neurological signals that are associated with the users' dynamic temporal cognitive response to the music. For example, analysts 118 may attempt to identify combinations of neurological signals that are statistically associated with the user feedback from users at at least a subset of locations 110. This may allow analysts 118 to determine sets of neurological signals that are associated with the user feedback, such as music that is 'sultry,' 'sexy' or 'sad.' Because music has cultural connotations, note that the collected data may include metadata, such as demographic and/or cultural information about the users, which may be used by analysts 118 when determining the sets of neurological signals.

After being 'trained' in this way, system 100 may provide an interactive music-performance platform in which brainwave data from one or more users or listeners is used to influence the score, pitch, or other musical performance attributes. Ideally, the performer/musical producer would have some idea of the neurological signals (such as electro-encephalogram biomarkers) that signify, in a user or in aggregate across a group of users, appreciation or enjoyment of a song. Using this information, the performer/producer may modify the performance in real time so as to maximize the presence of those neurological signals.

In another example, system 100 may be used to implement an interactive card or board game (such as poker), where the players are wearing electrode headsets and each has access to the brainwave data of the other players. The measured neurological signals could be used by a user to discern what type of poker hand a competitor has, i.e., to determine if the competitor is bluffing.

In yet another example, system 100 may be used to synchronize viewing of a political debate (or legal arguments in a court case) in which a large population of voters or potential jurors are wearing electrode headsets and their feedback (such as a positive/negative score) is recorded and aggregated at various points during the argument, thereby giving the debaters feedback on the relative effectiveness of their arguments.

Once the sets of neurological signals have been determined, they can be used to facilitate a variety of services. For example, the neurological signatures may be sold to market research organizations, so that these organizations can obtain neuromarketing data garnered in real time or historically from a large number of different users using different electrode configurations 112 (e.g., different models of brain-sensing devices).

In some embodiments, the neurological signals are measured after neurological stimuli are applied to the users, i.e., the users are first stimulated or driven using electrodes, and subsequently the neurological signals are synchronously or asynchronously measured. Furthermore, after the neurological signatures have been determined during a 'training' operating mode of system 100, these neurological signatures may be used open loop in various applications (such as software programs) that execute on electronic devices 108 to neurologically monitor and/or stimulate the users.

Figure 2:
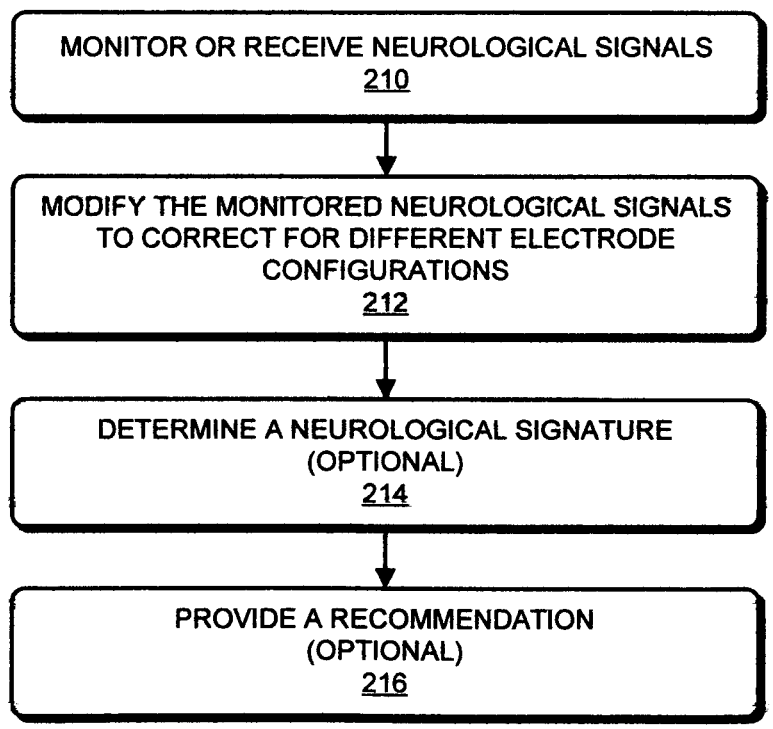
FIG. 2 is a flow chart illustrating a method for analyzing neurological signals in accordance with an embodiment of the present disclosure.

We now describe embodiments of an analysis technique. FIG. 2 presents a flow chart illustrating a method 200 for analyzing neurological signals, which may be performed by a system, such as server 114 in FIG. 1 or computer systems 900 in FIG. 9. During operation, the computer system monitors or receives neurological signals (operation 210) from users at multiple locations, where the neurological signals are associated with different electrode configurations. Then, the computer system modifies the monitored neurological signals to correct for the different electrode configurations (operation 212) so that a resulting set of modified neurological signals corresponds to a common electrode configuration, thereby facilitating subsequent identification of a subset of the set of modified neurological signals.

Note that the different electrode configurations may include: different types of electrodes, such as different electrode models provided by different manufacturers; different spatial sampling rates; and/or different electrode positions on the users.

Furthermore, the modifying (operation 212) may involve: interpolating between the monitored neurological signals associated with a pair of adjacent electrodes in a given electrode configuration; interpolating between the monitored neurological signals associated with the pair of adjacent electrodes in the given electrode configuration based on the neurological signals associated with at least another electrode in the given electrode configuration; extrapolating the monitored neurological signals associated with at least a subset of the electrodes is the given electrode configuration; implied data correlation; and/or duplication of at least some of the monitored neurological signals.

In some embodiments, the system optionally: determines a neurological signature (operation 214) characteristic of a behavior exhibited or performed by multiple individuals corresponding to the monitored neurological signals, where the neurological signature includes a subset of the set of modified neurological signals; and provides a recommendation (operation 216) to guide improvement of the behavior based on the neurological signature (such as a recommendation on how to modify the behavior to match the neurological signature of another individual who is healthier or who has better performance at a task). For example, the neurological signature may include particular EEG signals associated with a psychological or an emotional state, a thought and/or a physical activity. Thus, method 200 may be used to advance fields such as: personal training, sports training, psychology, psychiatry and education.

In some embodiments of method 200, there may be additional or fewer operations. For example, the set of modified neurological signals may be provided to third parties (such as analysts 118 in FIG. 1) for analysis. Note that these third parties may be other than an operator of server 114 in FIG. 1. Moreover, the order of the operations may be changed, and/or two or more operations may be combined into a single operation.

In an exemplary embodiment, the analysis technique is used to construct neurological signals associated with one or more virtual electrodes having the common electrode configuration. In the discussion that follows, EEG signals and EEG electrodes are used as art illustrative example.

Commercial EEG headsets come in a wide variety of shapes and sizes, and in a wide variety of configurations in terms of the number and placement of the electrodes. Consequently, different EEG headsets may read or sense data from different parts or regions of the brain. However, when analyzing the resulting EEG signals, it may be useful to read the electrode data that comes from a particular point on the brain.

When no physical electrode exists at a particular point (or when different headsets have different electrode configurations), a variety of techniques can be applied to construct approximated virtual electrode points, which may allow for a richer set of analysis techniques on a wider array of EEG hardware. In particular, interpolation, extrapolation, data duplication, correlative techniques and/or Green's function techniques may be used to construct one or more EEG signals corresponding to a virtual electrode from existing or predetermined EEG data.

EEG machines have been used since the 1920s. Since then, standards for electrode placement have been developed, which allows users (such as researchers) to communicate about EEG readings in a common way, as well as to share and build upon discoveries. Recently, EEG technology has been miniaturized and commoditized. In the process of miniaturization, many EEG systems have had to compromise on electrode (or sensor) placement, creating more portable but lower resolution EEG datasets. In order to be compatible with existing research or with higher-resolution EEG systems, EEG signals corresponding to a virtual electrode configuration can be determined for measured EEG signals associated with a real electrode configuration using techniques such as interpolation and/or extrapolation.

EEG data or signals are read from the electrical activity created by an aggregate of neurons underneath an individual's skull. Many factors can make interpolating virtual electrode data difficult. For example, the EEG signal voltages are often small. Moreover, based on Maxwell's equations, the voltage decreases with distance from the source (in this example, the neurons under the individual's skull). In addition to electrical signal drop-off, there is often a lack of sufficient data points and/or issues associated with the skull topography.

For example, the measurable voltage of EEG is typically very low, around −100 mV. This is usually lower than the voltage given off by muscles in the face (which may exceed −500 mV) or background noise (which may be even higher). Because both the EEG signal and electrical noise come in through the same electrode, isolating the EEG signal from the noise can be challenging.

Moreover, electrical signals or rates are exponential with distance and the distance between the electrodes in various EEG systems is often highly variable and can be very large (e.g., between 0.5 and 15 cm). Consequently, the electrical signals may not be shared between the electrodes. However, this can make it difficult to use interpolation techniques to isolate common signal properties between the electrodes to create a virtual electrode in the space(s) between the electrodes. In some embodiments, the spacing between electrodes needed to enable extrapolation or interpolation techniques is determined based on the impedance of the brain, skull, and/or skin.

Furthermore, there can also be a lack of sufficient data points. For example, in some cases, no reference electrodes exist to reliably isolate the intermediate signal, for instance at edge cases where a virtual electrode is being approximated near the outer-most physical electrode. Additionally, there are often challenges associated with the skull topography. In particular, the simplest interpolation techniques are usually best suited to planar models in which the incoming data points are mapped out perpendicular to the source of the data. This approach can be used in the magnification of digital photographs. Digital photos are typically represented by a flat, two-dimensional grid. By assuming that the light that created each pixel in the grid entered the camera perpendicular to the surface of the photograph, linear interpolation can be performed between a pair of pixels. New pixels may be created by assuming that each new pixel captures a percentage of the light from the pixel beside it. However, in comparison, the skull is curved and the electrical signals that create EEG signals can emanate from the three-dimensional space underneath the skull. In this example, it is possible that an EEG signal read by the placement of a virtual electrode may be imperceptible to the two (adjacent) electrodes, making interpolation difficult.

In the disclosed analysis technique, several approaches may be used to address the aforementioned problems, including: a Fourier transform (such as the Fast-Fourier Transform or FFT, spectral analysis, and more generally a transformation technique to and/or from the time domain to the frequency domain), interpolation, extrapolation, assumed data correlation and/or data duplication. The FFT is a mathematical analysis that converts a composite signal into its component frequencies. EEG records change in voltages over time, which typically is a composite between low frequency and high frequency periodic electrical signals. When this EEG signal is processed using the FFT, the composite frequencies and their amplitudes may be isolated. In particular, so-called alpha, beta, gamma, and and other brain waves may be isolated from an EEG signal. Note that determining or knowing the composite frequencies of an EEG signal may allow one or more of the other described techniques to be performed.

Figure 3:
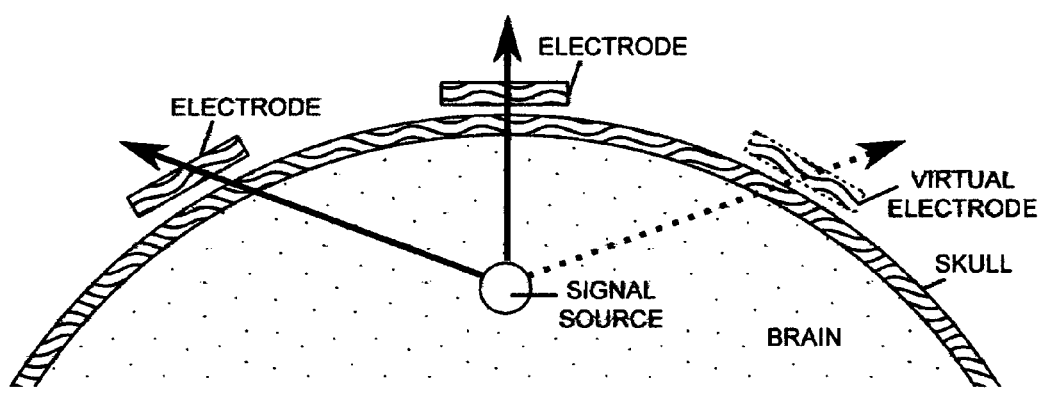
FIG. 3 is a drawing illustrating electrodes on the skull in accordance with an embodiment of the present disclosure.

As shown in FIG. 3, interpolation can be used to mathematically construct a virtual EEG electrode from existing physical electrode data. This approach may assume that some of the data that comes into the physical electrodes is shared with the virtual electrode. Although voltage drop off is rapid, much of EEG brainwave data is similar between electrodes. Consequently, interpolation can produce reasonable facsimiles of the data that would be under a real electrode. In principle, the more real data points one has, and the closer they are together, the more accurate the interpolation can be. Depending on the accuracy, speed, and memory constraints, local and/or global interpolation may be performed. Local interpolation may take into account neighboring electrodes (such as adjacent pairs of electrodes), while global interpolation may take into account more of or all of the available electrodes.

Figure 4:
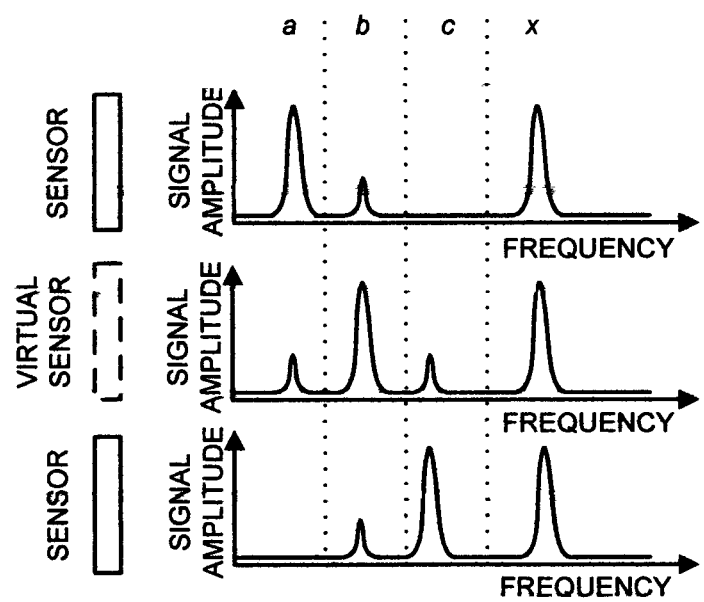
FIG. 4 is a drawing illustrating a local interpolation technique in accordance with an embodiment of the present disclosure.

As shown in FIG. 4, with local interpolation, a virtual EEG signal can the created using a weighted average of the measured EEG signals from two nearby or adjacent electrodes. The weighted average can take into account the voltage drop-off over distance. This can be expressed as $$s_v = \sum_{n=0}^{32} s_1 f(d_1) s_2 f(d_2),$$

where $s_v$ is the virtual electrode signal, $s_1$ is the electrode signal 1 at frequency n, $s_2$ is the electrode signal 2 at frequency n, $f(d_1)$ is the voltage drop off as a result of distance from electrode 1, $f(d_2)$ is the voltage drop off as a result of distance from electrode 2. In this way, the virtual electrode may magnify common frequencies that are presumably created underneath the virtual electrode (e.g., frequency b). Note that frequencies unique to the real electrodes that are presumably created closer to them may be diminished (e.g., frequencies a and c). Furthermore, frequencies that are common to both electrodes may be maintained (e.g., frequency x).

Figure 5:
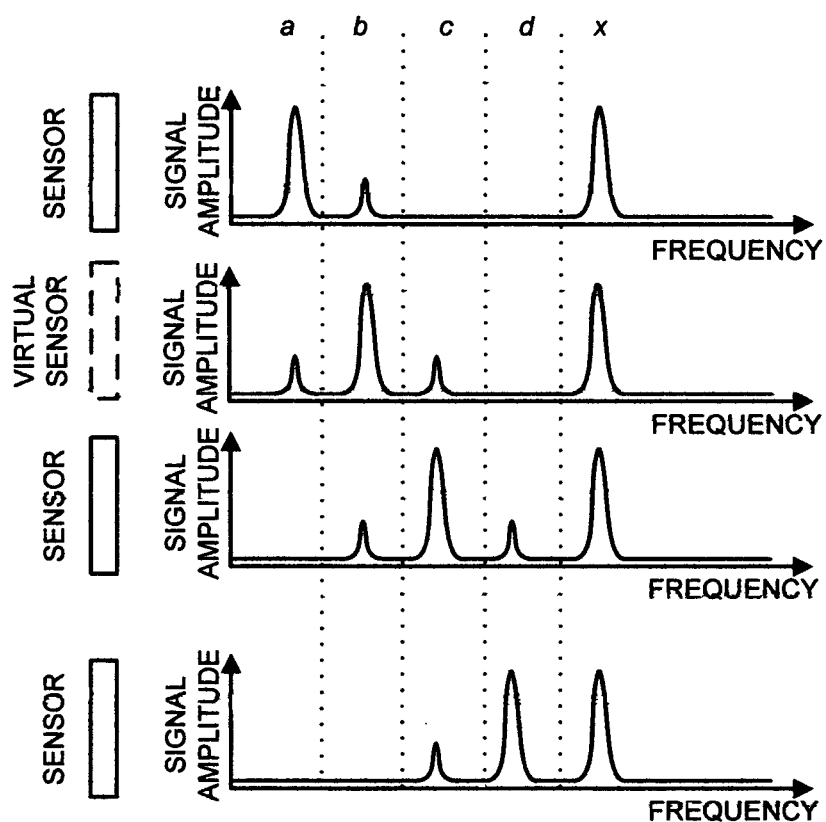
FIG. 5 is a drawing illustrating a global interpolation technique in accordance with an embodiment of the present disclosure.
Figure 6:
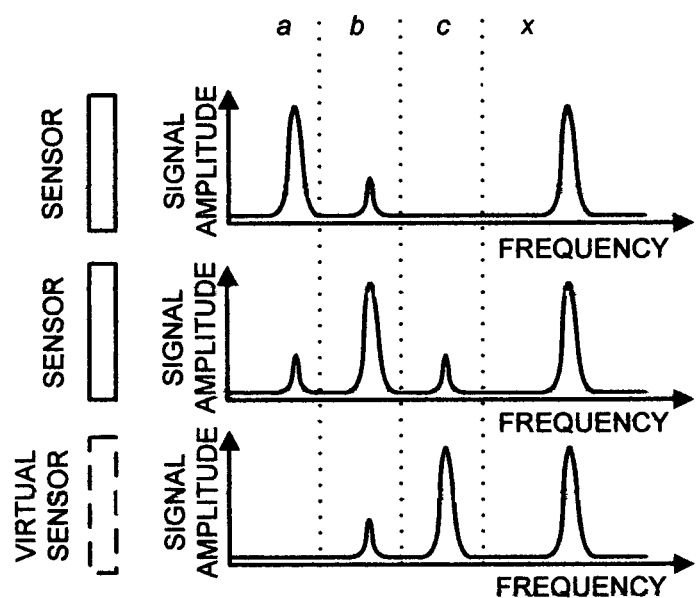
FIG. 6 is a drawing illustrating an extrapolation technique in accordance with an embodiment of the present disclosure.
Figure 7:
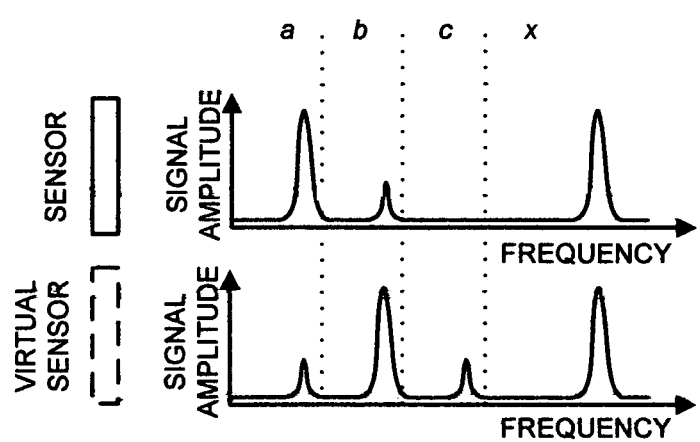
FIG. 7 is a drawing illustrating an implied-data-correlation technique in accordance with an embodiment of the present disclosure.
Figure 8:
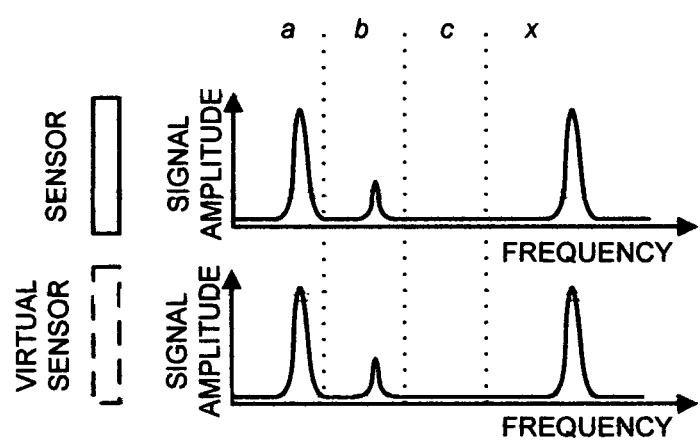
FIG. 8 is a drawing illustrating a signal-duplication technique in accordance with an embodiment of the present disclosure.

However, local interpolation usually only accounts for EEG signals that are shared between two real electrodes and the third virtual electrode between or adjacent to them. In order to account for electrode signals originating outside the two electrodes in question, the electrode configuration illustrated in FIG. 5 can be used. By taking into account electrode data outside the neighboring electrodes, more accurate data can be constructed because nearby electrode data can be isolated and removed. This can be expressed as $$s_v = \sum_{s=0}^{k} \sum_{n=0}^{32} s_s f(d_s),$$

where $s_v$ is the virtual electrode signal, $s_1$ is the electrode signal s at frequency n, k is the total number of electrode, $f(d_s)$ is the voltage drop off as a result of distance from electrode s. In this way, the virtual electrode may have the interpolative properties of local interpolation, but may also eliminate frequencies that originate from non-nearby sources (e.g., frequency d).

Note that the virtual electrodes may not always lie between real electrodes. In particular, some may be outside the bounds of the physical electrodes as illustrated in FIG. 3. In this case, extrapolation may be used to construct the virtual EEG signals. In the extrapolation technique, a virtual electrode may magnify the signals from a nearby electrode, but may subtract the signals from a remote or distant electrode. This can be expressed as $$s_v = \sum_{s=0}^{k} \sum_{n=1}^{32} \frac{1}{s_s} f(d_s)$$

where $s_v$ is the virtual electrode signal, $s_1$ is electrode signal s at frequency n, k is the total number of electrodes, and $f(d_s)$ is the voltage drop off as a result of distance from electrode s.

There may be circumstances in which a virtual electrode is known to produce certain frequencies, so a virtual signal can be constructed using known properties. An example of this may occur during stress or concentrations, when beta waves (16-32 Hz) are amplified. If beta wave frequencies have already been established at around, e.g., 18-22 Hz in a particular person on a real electrode, then it may be possible to use proxy information about stress or corroborating electrode signals to detect brain events and to construct a frequency pattern that is indicative of that brain event on the virtual electrode. For example, an assumed beta wave frequency range of 18-22 Hz may be created. In particular, $g=100-25(x-20)^2$, where g is the generated signal (e.g., 100 mV between 18-22 Hz). By taking into account nearby electrode data using an extrapolation technique, a reasonable facsimile of the electrode data can be constructed. This can be expressed as $$s_v = g + \sum_{s=0}^{k} \sum_{n=1}^{32} \frac{1}{s_s} f(d_s),$$

where $s_v$ is the virtual electrode signal, $s_1$ is the electrode signal s at frequency n, k is the total number of electrodes, and $f(d_s)$ is the voltage drop off as a result of distance from electrode s. The resulting signal may include both the generated beta wave and the extrapolated nearby electrode data.

During signal duplication may be a technique of last resort for virtual electrode construction. In particular, when the virtual electrode is close to the real electrode, no reasonable correlative properties exist between the two electrodes, and no other signal information is present, it may be useful to duplicate the EEG signals from a real electrode. For example, it may be practical to use signal duplication on opposite points of the prefrontal cortex for measurements of stress, where comparative analysis is not necessarily used. In this case, the virtual signal can be constructed as $$s_v = \sum_{n=1}^{32} s,$$

where $s_v$ is the virtual electrode signal, s is real electrode signal at frequency n, and k is the total number of electrodes.

Thus, by knowing the relationship between physical electrodes and the radius of their ability to sense electrical impulses, the appropriate technique may be selected to construct, interpolate, and/or extrapolate virtual electrode data. As more commercial EEG systems are available, it may become useful to have virtual EEG electrode configurations to bridge the gap between hardware designs and implementations. Note that a common EEG electrode configuration may allow consumers and developers to be more platform-agnostic, freeing them to choose hardware based on their usage needs rather than solely based on what software analysis can be performed on a piece of hardware.

In some embodiments, when the locations of electrodes on the surfaces of individuals' heads in at least some commercial headsets is not standardized, the monitored neurological signals are modified to correct for the different electrode configurations, so that a resulting set of modified neurological signals corresponds to a common electrode configuration (which have a common set of locations or geometry for the electrodes). In particular, the bioelectric impressed current densities associated with the different electrode configurations can be calculated by inverting an equation representing the neurological signals associated with the bioelectric impressed current densities based on the measured neurological signals (such as EEG signals) and the geometry of their associated electrode configurations. Then, the calculated bioelectric impressed current densities and the geometry of the common electrode configuration can be used in this equation to determine the set of modified neurological signals corresponds to the common electrode configuration (e.g., EEG signals at the common set of location for the electrodes in the common electrode configuration). Alternatively or additionally, a Green's function technique may the used to determine the set of modified neurological signals corresponds to the common electrode configuration based on the calculated bioelectric impressed current densities and the geometry of the common electrode configuration.

Figure 9:
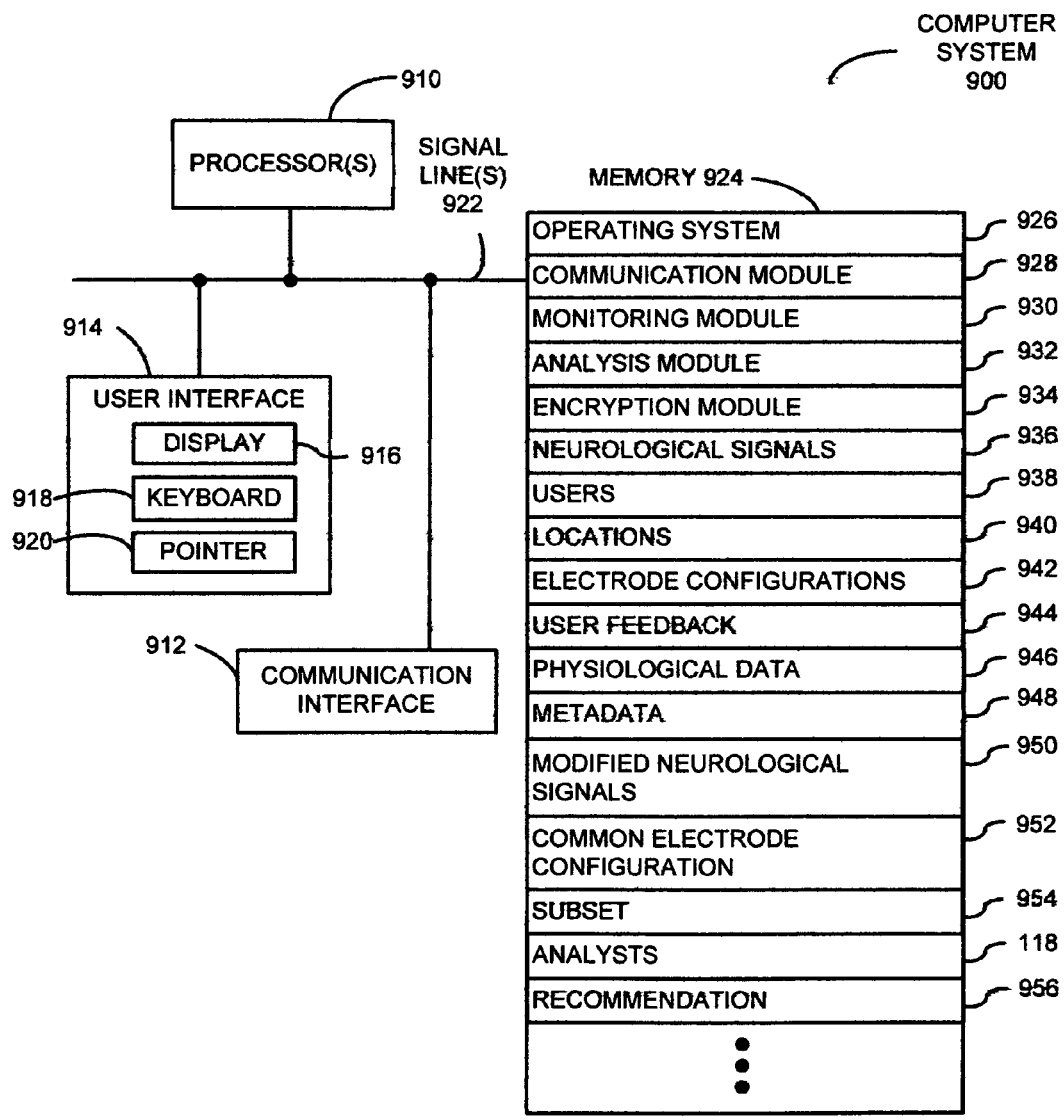
FIG. 9 is a block diagram illustrating a computer system in the system of FIG. 1 in accordance with an embodiment of the present disclosure.

FIG. 9 presents a block diagram illustrating a computer system 900 (such as server 114 in FIG. 1) that performs method 200 (FIG. 2). Computer system 900 includes one or more processing units or processors 910, a communication interface 912, a user interface 914, and one or more signal lines 922 coupling these components together. Note that the one or more processors 910 may support parallel processing and/or multi-threaded operation, the communication interface 912 may have a persistent communication connection, and the one or more signal lines 922 may constitute a communication bus. Moreover, the user interface 914 may include: a display 916, a keyboard 918, and/or a pointer 920, such as a mouse.

Memory 924 in computer system 900 may include volatile memory and/or non-volatile memory. More specifically, memory 924 may include: ROM, RAM, EPROM, EEPROM, flash memory, one or more smart cards, one or more magnetic disc storage devices, and/or one or more optical storage devices. Memory 924 may store an operating system 926 that includes procedures (or a set of instructions) for handling various basic system services for performing hardware-dependent tasks. Memory 924 may also store procedures (or a set of instructions) in a communication module 928. These communication procedures may be used for communicating with one or more computers and/or servers, including computers and/or servers that may be remotely located with respect to computer system 900.

Memory 924 may also include multiple program modules (or sets of instructions), including: monitoring module 930 (or a set of instructions), analysis module 932 (or a set of instructions) and/or encryption modules 934 (or a set of instructions). Note that one or more of these program modules (or sets of instructions) may constitute a computer-program mechanism.

During method 200 (FIG. 2), monitoring module 930 monitors (or receives via communication interface 912 and communication module 928) neurological signals 936 from users 938 at locations 940, where neurological signals 936 are associated with different electrode configurations 942. In addition, monitoring module 930 may collect: user feedback 944, physiological date 946, and/or metadata 948.

Then, analysis module 932 modifies neurological signals 936 to correct for different electrode configurations 942 so that a resulting set of modified neurological signals 950 corresponds to a common electrode configuration 952, thereby facilitating subsequent identification of a subset 954 of set of modified neurological signals 950 (such as a neurological signature), for example, by analysts 118. Alternatively or additionally, subset 954 of set of modified neurological signals 950 may be identified by analysis module 932. In addition, computer system 900 may provide a recommendation 956 (via communication module 928 and communication interface 912) based on subset 954.

Figure 10:
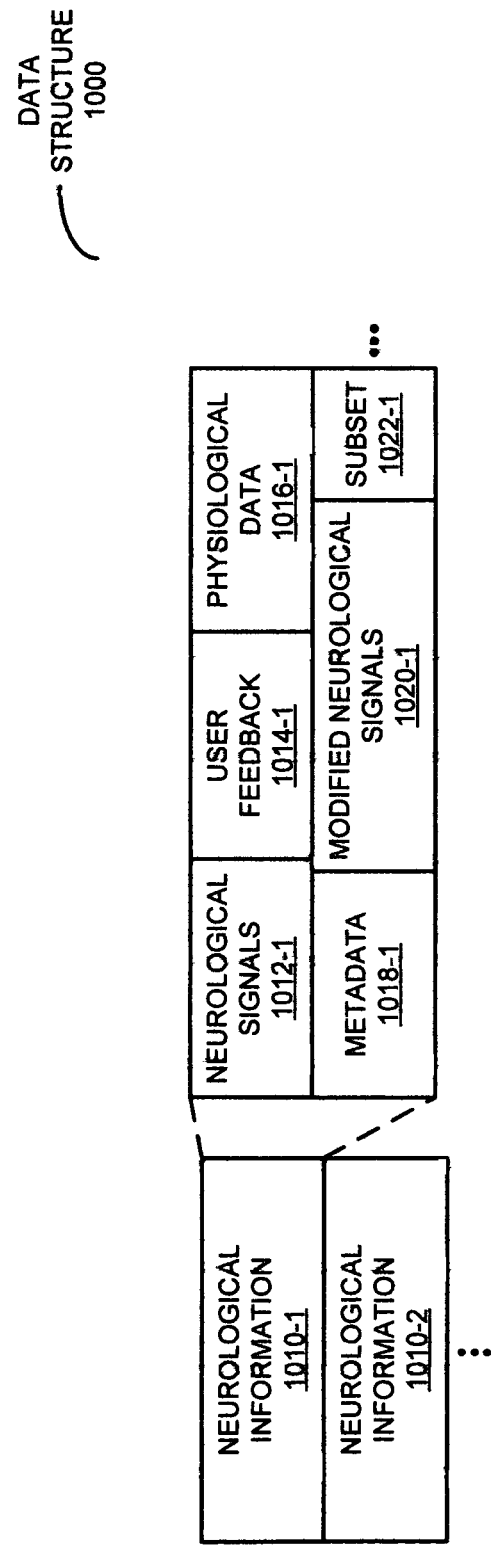
FIG. 10 is a block diagram illustrating a data structure for use in the computer system of FIG. 9 in accordance with an embodiment of the present disclosure.

As shown in FIG. 10, which illustrates a data structure 1000, the measured and modified neurological signals may be aggregated for use by analysts 118 (FIGS. 1 and 9). For example, neurological information 1010-1 may include: neurological signals 1012-1, user feedback 1014-1, physiological data 1016-1, metadata 1018-1, modified neurological signals 1020-1, and/or subset 1022-1 of modified neurological signals 1020-1.

Referring back to FIG. 9, instructions in the various modules in memory 924 may be implemented in: a high-level procedural language, an object-oriented programming language, and/or in an assembly or machine language. Note that the programming language may be compiled or interpreted, e.g., configurable or configured, to be executed by the one or more processors 910.

Although computer system 900 is illustrated as having a number of discrete items, FIG. 9 is intended to be a functional description of the various features that may be present in computer system 900 rather than a structural schematic of the embodiments described herein. In practice, and as recognized by those of ordinary skill in the art, the functions of computer system 900 may be distributed over a large number of servers or computers, with various groups of the servers or computers performing particular subsets of the functions. In some embodiments, some or all of the functionality of computer system 900 may the implemented in one or more application-specific integrated circuits (ASICs) and/or one or more digital signal processors (DSPs).

Electronic devices, computers and servers in systems 100 (FIG. 1) and/or computer system 900 may include one of a variety of devices capable of manipulating computer-readable data or communicating such data between two or more computing systems over a network, including: a personal computer, a laptop computer, a tablet computer, a mainframe computer, a portable electronic device (such as a cellular phone or PDA), a server and/or a client computer (in a client-server architecture). Moreover, network 116 (FIG. 1) may include: the Internet, World Wide Web (WWW), an intranet, a cellular-telephone network, LAN, WAN, MAN, or a combination of networks, or other technology enabling communication between computing systems.

System 100 (FIG. 1), computer system 900, and/or data structure 1000 (FIG. 10) may include fewer components or additional components. Moreover, two or more components may be combined into a single component, and/or a position of one or more components may be changed. In some embodiments, the functionality of computer system 900 may be implemented more in hardware and less in software, or less in hardware and more in software, as is known in the art.

The foregoing description is intended to enable any person skilled in the art to make and use the disclosure, and is provided is the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown, but is to be accorded the widest scope consistent with the principles and features disclosed herein.

What is claimed is:

1. A computer-implemented method for analyzing neurological signals, comprising:
monitoring neurological signals from users at multiple separate locations, wherein the neurological signals are associated with different electrode configurations;
using a computer, modifying the monitored neurological signals to correct for the different electrode configurations so that a resulting set of modified neurological signals corresponds to a common electrode configuration so that a subset of the set of modified neurological signals can be identified,
wherein the modifying involves at least one of: interpolating between the monitored neurological signals associated with a pair of adjacent electrodes in a given electrode configuration; interpolating between the monitored neurological signals associated with the pair of adjacent electrodes in the given electrode configuration based on the neurological signals associated with at least another electrode in the given electrode configuration; extrapolating the monitored neurological signals associated with at least a subset of the electrodes in the given electrode configuration; implied data correlation; and duplication of at least some of the monitored neurological signals;
determining a neurological signature characteristic of a behavior exhibited or performed by multiple individuals corresponding to the monitored neurological signals, wherein the neurological signature includes a subset of the set of modified neurological signals; and
providing a recommendation that guides improvements of the behavior based on the neurological signature.

2. The method of claim 1, wherein the different electrode configurations include different types of electrodes.

3. The method of claim 1, wherein the different electrode configurations include different electrode models provided by different manufacturers.

4. The method of claim 1, wherein the different electrode configurations include different spatial sampling rates.

5. The method of claim 1, wherein the different electrode configurations include different electrode positions on the users.

6. The method of claim 1, wherein the neurological signals include electroencephalogram signals.

7. The method of claim 1, wherein the method further comprises analyzing the modified neurological signals based on physiological responses of the users to external stimuli to identify the subset of the set of modified neurological signals.

8. A computer-program product for use in conjunction with a computer system, the computer-program product comprising a non-transitory computer-readable storage medium and a computer-program mechanism embedded therein, to analyze neurological signals, the computer-program mechanism including:
instructions for monitoring neurological signals from users at multiple separate locations, wherein the neurological signals are associated with different electrode configurations;
instructions for modifying the monitored neurological signals to correct for the different electrode configurations so that a resulting set of modified neurological signals corresponds to a common electrode configuration so that a subset of the set of modified neurological signals can be identified,
wherein the modifying involves at least one of: interpolating between the monitored neurological signals associated with a pair of adjacent electrodes in a given electrode configuration; interpolating between the monitored neurological signals associated with the pair of adjacent electrodes in the given electrode configuration based on the neurological signals associated with at least another electrode in the given electrode configuration; extrapolating the monitored neurological signals associated with at least a subset of the electrodes in the given electrode configuration; implied data correlation; and duplication of at least some of the monitored neurological signals;
instructions for determining a neurological signature characteristic of a behavior exhibited or performed by multiple individuals corresponding to the monitored neurological signals, wherein the neurological signature includes a subset of the set of modified neurological signals; and
instructions for providing a recommendation that guides improvement of the behavior based on the neurological signature.

9. The computer-program product of claim 8, wherein the different electrode configurations include different types of electrodes.

10. The computer-program product of claim 8, wherein the different electrode configurations include different electrode models provided by different manufacturers.

11. The computer-program product of claim 8, wherein the different electrode configurations include different spatial sampling rates.

12. The computer-program product of claim 8, wherein the different electrode configurations include different electrode positions on the users.

13. The computer-program product of claim 8, wherein the neurological signals include electroencephalogram signals.

14. The computer-program product of claim 8, wherein the computer-program mechanism further includes instructions for analyzing the modified neurological signals based on physiological responses of the users to external stimuli to identify the subset of the set of modified neurological signals.

15. A computer system, comprising:
a processor;
memory; and
a program module, wherein the program module is stored in the memory and configurable to be executed by the processor to analyze neurological signals, the program module including:
instructions for monitoring neurological signals from users at multiple separate locations, wherein the neurological signals are associated with different electrode configurations;
instructions for modifying the monitored neurological signals to correct for the different electrode configurations so that a resulting set of modified neurological signals corresponds to a common electrode configuration so that a subset of the set of modified neurological signals can be identified,
wherein the modifying involves at least one of: interpolating between the monitored neurological signals associated with a pair of adjacent electrodes in a given electrode configuration; interpolating between the monitored neurological signals associated with the pair of adjacent electrodes in the given electrode configuration based on the neurological signals associated with at least another electrode in the given electrode configuration; extrapolating the monitored neurological signals associated with at least a subset of the electrodes in the given electrode configuration; implied data correlation; and duplication of at least some of the monitored neurological signals;
instructions for determining a neurological signature characteristic of a behavior exhibited or performed by multiple individuals corresponding to the monitored neurological signals, wherein the neurological signature includes a subset of the set of modified neurological signals; and
instructions for providing a recommendation that guides improvement of the behavior based on the neurological signature.

16. The computer system of claim 15, wherein the different electrode configurations include different types of electrodes.

17. The computer system of claim 15, wherein the different electrode configurations include different electrode models provided by different manufacturers.

18. The computer system of claim 15, wherein the different electrode configurations include different spatial sampling rates.

19. The computer system of claim 15, wherein the different electrode configurations include different electrode positions on the users.

20. The computer system of claim 15, wherein the neurological signals include electroencephalogram signals.

* * * * *